United States Patent [19]

Roelz et al.

[11] Patent Number: 4,769,390
[45] Date of Patent: Sep. 6, 1988

[54] WASHABLE TOPICAL PREPARATION FOR TREATING PSORIASIS

[75] Inventors: Wolfgang Roelz, Langen-Neurott; Josef Mueller, Lindenfels, both of Fed. Rep. of Germany

[73] Assignee: Rohm GmbH Chemische Fabrik, Darmstadt, Fed. Rep. of Germany

[21] Appl. No.: 5,845

[22] Filed: Jan. 21, 1987

[30] Foreign Application Priority Data

Feb. 7, 1986 [DE] Fed. Rep. of Germany ....... 3603859

[51] Int. Cl.$^4$ ............................................. A61K 31/17
[52] U.S. Cl. .................... 514/588; 514/732; 514/863
[58] Field of Search .................. 514/588, 732, 863

[56] References Cited

U.S. PATENT DOCUMENTS 4,291,062 9/1981 Leigh et al. ........................ 514/588
4,551,480 11/1985 Stiefel et al. ........................ 514/680

FOREIGN PATENT DOCUMENTS 2113547 8/1983 United Kingdom .
2157173 10/1985 United Kingdom .

Primary Examiner—Leonard Schenkman
Attorney, Agent, or Firm—Oblon, Fisher, Spivak, McClelland & Maier

[57] ABSTRACT

A pharmaceutical preparation for topical treatment of skin disorders, particularly psoriasis, comprising active ingredients consisting essentially of combinations of 1,8,9-anthracenetriol, and/or derivatives thereof, and urea. The subject preparation is applied in an essentially water-free excipient. The preparation includes surfactants, which are ordinarily incompatible with the active ingredients. By the use of surfactant-urea combinations, surfactants can be incorporated into a stable, lipophilic pharmaceutical preparation, whereby after use the surfactants are liberated by the action of water, to form a readily washable emulsion system. The inventive preparation is advantageously used in the "short time" method of therapy of psoriasis.

5 Claims, No Drawings

WASHABLE TOPICAL PREPARATION FOR TREATING PSORIASIS

BACKGROUND OF THE INVENTION

1. Field of the Invention

The present invention relates to pharmaceutical preparations for treating psoriasis comprising a combination of substances based on 1,8,9-anthracenetriol and urea. The preparations are particularly useful for treating psoriasis on the head and other hairy body parts, by the method of short-time therapy.

2. Description of the Related Art

Psoriasis is among the dermatoses having a poorly understood etiology. The therapies of choice are thus topical agents such as salicyclic acid, tars (pices var.), vitamin A acid, corticosteroids, etc. Sometimes, coal tar is used.

Among the agents long used for treating psoriasis is 1,8,9-anthracenetriol (also called dithranol or Anthralin), and certain of its acyl derivatives, usually in preparations containing 0.1–5% by weight of this agent.

The only pharmaceutical forms in which the therapeutic agents are available are lipophilic preparations for local therapy, due to the high instability of the active ingredients against air, oxygen, water, and alkalies. These strongly fattening preparations have relatively low storage stability. They are necessarily inconvenient to use because clothing as well as washrags are strongly dyed by the active ingredient, dithranol. Further, the hydrophobic preparations are difficult to wash off of the skin, particularly in hairy areas.

A psoriasis patient's use of the customary preparations (which were intended for treating non-hairy parts of the skin) in hairy parts leads to a number of problems. If an ointment comprising Vaseline, salicylic acid (2–3%), and dithranol (0.5–3%) is used on, e.g. skin in the hairy area of the head, vigorous rubbing is needed to provide proper contact. This rubbing causes appreciable pain to the affected skin, which already has lesions. Further, due to complications, the treatment must often be performed by hospital personnel.

An optimal therapeutic preparation for treating psoriasis should enable concurrent action of urea and dithranol (Eur. A No. 6,724). It is probable that the antipsoriatic action is not solely due to dithranol. Clinical research indicates that the urea, via its multiple effects such as keratolysis and horny layer (stratum corneum) hydration, which effects are known, acts on the epidermis to ameliorate the interference with proper epithelial formation caused by psoriasis.

Another important consideration in treating psoriasis is the desirability of dissolving scaly formations, and of moisturizing the dried horny layer. Urea plays an important part in this. By its keratolytic action it facilitates sloughing off of scaly formations (Ernst, T.-M., 1981, *Z. Hautkrankheiten*, 56, 18:1197–1206). Further, urea has hydrating capability, promoting improved water uptake by the horny layer, which substantially ameliorates symptoms, particularly in psoriasis patients.

Studies of the penetration kinetics of dithranol have shown that the substance penetrates much faster into the damaged skin of psoriasis lesions than into normal skin. This suggests a technique of treating psoriasis whereby after a short period of application of a topical dithranol preparation, the residue on the surface is removed, thereby substantially reducing the amount of dithranol which penetrates to healthy skin. The side effects such as strong skin irritation and reddening suffered by healthy skin are thus appreciably avoided. These side effects often lead to interruption of therapy. The therapeutic results of this short time therapy (which was called "minute therapy" by Runne and Kunze) were judged equal to those of classical long-term application of dithranol preparations (Runne, U. and Kunze, J., 1982. *Brit. J. Dermatol.*, 106:135–139; and 1985, *Der Hautartzt*, 36:44–46).

A prerequisite for the above-described therapy ("minute therapy") is good removability of the preparation employed. There is no suitable preparation available which has an active life of typical length required for commercial distribution, and which can be readily removed. Accordingly, one resorts to a second, inert creme, which is used to apply the material; and then this is removed with detergents. In order to facilitate wide use of the "minute therapy" for treating psoriasis, particularly in hairy areas of the body, there is a need for a topical preparation which allows the time of exposure to be accurately controlled by removing said preparation by simple rinsing.

SUMMARY OF THE INVENTION

Accordingly, it is an object of the present invention to provide a topical preparation of a skin-treating composition which can be readily removed from the skin by simple rinsing.

It is a further object of this invention to provide a topical preparation which allows the time of exposure to be accurately controlled by removing the preparation by simple rinsing.

It is yet another object of this invention to provide a method for treating psoriasis with a topical preparation which can be readily removed from the skin by simple rinsing.

The above and other objects have been achieved by a combination of two materials having synergistic action.

The inventive combination is comprised of the following active ingredients:

(A) 1,8,9-Anthracenetriol and/or derivatives of same; and (B) Urea, in a fine crystalline form suitable for topical therapy (hereinafter, "microdisperse urea").

Further, the novel forms of administration are characterized in that they can be readily washed away from the site of application following a short, controlled action period. If, e.g. lipid systems are used, a relatively high content of surfactants is required. Many surfactants, ethoxylated and ionic, are incompatible with dithranol and with urea, however (DAC, 1979), and cannot be used as ingredients in products which are to be storage-stable.

DETAILED DESCRIPTION OF THE PREFERRED EMBODIMENTS

According to the invention, the destabilizing action of surfactants on dithranol, particularly in the presence of water and under unfavorable pH conditions (particularly alkaline conditions), is impeded if the surfactants and detergent substances (which are usually substances with linear polar molecules) are added to the preparation in the form of urea inclusion compounds. These can be prepared in known fashion, either in the liquid phase or by suitable solid reactions. The surfactants, which are ordinarily available in aqueous pastes or water-containing highly viscous liquids, are thereby converted to a water-free form, yielding a stable, water-free pharmaceutical.

Following a controlled therapeutic action period, which is shorter than that for known products, the preparation can be completely removed by the use of water, such as by simple rinsing accompanied by extremely gentle massage. The addition of water results in the formation of an oil-in-water emulsion, which can be made less viscous with water and thereby is easily removable. Even after use on hairy body parts, the medicament can be removed without additional use of a shampoo. It is noted that in the process, superfluous skin scales are also removed, due to the combination of the surfactant and the keratolytically acting urea.

The inventive therapeutic preparations are outstanding in that they can be used without having to be vigorously rubbed into the psoriatic skin areas (which are sensitive to the touch). This is particularly advantageous in the case of application to cephalic skin and other hairy regions of the body. Due to the type of preparation, which may be characterized as self-emulsifying, the inventive preparations can generally be easily removed by washing them off of the site of application.

It is particularly significant that the particular method of preparation and the composition of the inventive therapeutic preparations enables them to have the usual storage-stability of commercial preparations while combining into one preparation the oxidation-susceptible and hydrolysis-susceptible materials dithranol (and/or its derivatives) and urea, along with a high content of hydrophilic surfactants. Such stable preparations achieve standard storage-stability, under easy to maintain storage conditions (in particular, without cold storage) and without salicylic acid.

Also significant is the fact that the preparation is a single composition. It does not require patient preparation prior to use, by combining two prepreparations as described in Ger. OS No. 33 02 739. Nor does it require more than one agent to remove it after use.

Specific water-free forms of administration according to the invention include the following:
(a) Washable ointments.
(b) Cleansing creams and hair treating oils.
(c) Hydrophilic, self-emulsifying oil preparations.
(d) Hydrophilic cleansing oils.
(e) Washable massage oils and creams.
(f) Water-free oil bubble bath.

The technology for manufacturing such preparations is described in detail in "Ullmann's Encyklopaedie der technischen Chemie", 3rd Ed., Vol. 4, pp. 20–23; 4th Ed., Vol. 10, pp. 31–39; and 4th Ed., Vol. 12, pp. 557–566.

The inventive therapeutic preparations generally contain Component A in an amount of 0.1–5 wt. %, preferably 0.5–3 wt. %. Components A and B are generally present in the inventive preparations in a weight ratio of 1:1 to 1:100, preferably 1:2 to 1:25.

Various components may be used as consistency agents for the preparations (which are to have various viscosities). These include hydrocarbons (oleaginous to waxy; e.g. paraffin oils, polyethylenes with molecular weight up to 1,000), esters of fatty acids with long chain alcohols (e.g., oleic acid oleyl ester (Cetiol®)), esters of relatively long chain fatty acids or higher fatty acids (e.g., myristic acid or oleic acid) with alcohols having e.g., 1 to 4 C atoms, esterified polyvalent alcohols (e.g., glycerine or sorbitols), and long chain fatty alcohols (e.g., myristyl alcohol). The active ingredients—dithranol or derivatives, and the surfactant-urea inclusion compound—are incorporated into these consistency agent materials by known techniques. Additional dermatologically active substances may also be used if desired.

The surfactant-urea inclusion compound is prepared separately, by any of a number of known methods for preparing urea inclusion compounds, e.g. by mixing methanolic and/or aqueous surfactant solutions with urea, followed by crystallization; or by a solvent-free technique employing a suitable solid reaction, e.g. by trituration.

According to the invention, the surfactants which form inclusion compounds with urea include nearly-straight-chain hydroxyethoxy compounds, which are nonionic compounds which are water-soluble (HLB values of ca. 8 to 15) and can be separated from the inclusion compounds after application, by the use of water, which results in an oil-water emulsion. (For discussions of the concept of HLB values, and nonionic surfactants, see "Ullmann's", cited above, 4th Ed., Vol. 22, pp. 488 ff.) Examples of such compounds are polyoxyethylene (20) cetyl stearyl ether, CTFA name "Ceteareth-20", or diethylene glycol monolauryl ether, CTFA name "Laureth-2". (CTFA is the Cosmetic, Toiletry, and Fragrance Association, Washington, D.C.) These surfactants form inclusion compounds with urea, forming a hexagonal urea structure, as shown by X-ray studies. Hydroxyethoxy surfactants with a plurality of long straight chain groups branching from a structure such as that of sorbitan also display the inventive properties when combined with urea, but the surfactant-urea adducts are amorphous under X-ray examination. Their structure is not well understood. Possibly the long straight chain parts of the molecules are included in urea structures, while the more voluminous parts, particularly the branched parts, do not form urea adducts. The branched type of surfactants includes, e.g.: polyoxyethylene (20) sorbitan trioleate (commercially available as Tween® 85); polyoxyethylene sorbitol hexaoleate (Arlatone® T and G-1086, supplied by Atlas Chemie); and "PEG-7-glyceryl-cocoate", a polyoxyethylene-glycerine fatty acid ester.

The preparations may also contain other, non-ethoxylated, nonionic compounds, e.g. serving as emulsifiers or crosslinking agents, with HLB values in the range of about 0 to 9. Examples of such compounds are esters of glycerine (e.g., glycerine monostearate), or esters of sorbitan (e.g. sorbitan trioleate—commercially available as Span® 85). Other examples may be obtained from "Ullman's", cited above, Vol. 22, p. 489, which is incorporated herein by reference.

EXAMPLES

General Manufacturing Conditions for the Formulation Examples

The fatty phases are heated, along with added surfactants, to above the melting point, are degassed under vacuum, and are gassed with nitrogen. At temperatures below 50° C., the dithranol and urea (as surfactant-urea inclusion compounds and/or as a surfactant-urea "adduct") are added and are very finely dispersed by means of a wet comminuting apparatus, followed by rapid cooling to room temperature. The result is easily dispersible oils or pastes, which after therapeutic application can be readily and completely removed by washing with water.

| Exemplary Formulas: | Parts by weight |
|---|---|
| Water-Free Washable Massage Cream | |
| Myristyl alcohol | 40.0 |
| Coconut oil fatty alcohol caprylate and/or caprate | 15.0 |
| White Vaseline | 28.7 |
| Ceteareth-20 | 4.0 |
| Urea | 12.0 |
| Dithranol | 0.3 |
| | 100.0 |

(The Ceteareth-20 and urea are combined as a surfactant-urea inclusion compound.)

| Hydrophilic Oil: | |
|---|---|
| Viscous paraffin oil | 80.0 |
| Hard paraffin | 4.5 |
| Sorbitan trioleate (Span ® 85) | 1.5 |
| Polyoxyethylene sorbitan trioleate (Tween ® 85) | 3.5 |
| Urea | 10.0 |
| Dithranol | 0.5 |
| | 100.0 |

(The Tween ® 85 and urea are combined as a surfactant-urea "adduct".)

| Hydrophilic Oil: | |
|---|---|
| Cetiol ® | 31.0 |
| Isopropyl myristate | 24.5 |
| PCL liquidum (Pur-Zellin-Oel, supplied by the firm Dragoco) | 19.0 |
| Octyldodecanol | 10.0 |
| Polyoxyethylene sorbitol hexaoleate (Arlatone ® T) | 6.0 |
| Polyoxyethylene sorbitol hexaoleate (G.-1086) | 1.5 |
| Urea | 5.0 |
| Dithranol | 3.0 |
| | 100.0 |

(The sorbitol derivatives and urea are combined as a surfactant-urea "adduct".)

| Hydrophilic Cleansing Oil, Inclusion Compound Formulation: | |
|---|---|
| Isopropyl myristate | 40.0 |
| Liquid paraffin | 20.8 |
| Octyldodecanol | 20.0 |
| Hardened castor oil | 5.0 |
| Laureth-2 | 4.0 |
| Urea | 10.0 |
| Dithranol | 0.2 |
| | 100.0 |

(The Laureth-2 and urea are combined as a surfactant-urea inclusion compound.)

| Hydrophilic Cleaning Oil, "Adduct" Formulation: | |
|---|---|
| Isopropyl Myristate | 40.0 |
| Liquid paraffin | 14.0 |
| Octyldodecanol | 25.5 |
| Glycerine monostearate | 3.0 |
| PEG-7-glyceryl-cocoate | 5.0 |
| Urea | 12.0 |
| Dithranol | 0.5 |
| | 100.0 |

(The PEG derivative and urea are combined as a surfactant-urea "adduct.")

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A pharmaceutical preparation for topical treatment of skin disorders, comprising active ingredients consisting essentially of 1,8,9-anthracenetriol or derivatives thereof, and urea; wherein said urea is present in said preparation as a fine crystalline water-soluble surfactant-urea inclusion compound or as a water-soluble surfactant-urea adduct, wherein said anthracenetriol active ingredient is contained in an amount of from 0.1 to 5 wt. %, and said anthracenetriol contains the urea as a water-soluble surfactant-urea combination in an amount which is 1 to 100 times the amount by weight of the anthracenetriol component, and wherein the ratio of surfactant to urea ranges from 1:3 to 1:0.66.

2. A pharmaceutical preparation according to claim 1, wherein said surfactant in the surfactant-urea combination is an ethoxylated compound with an HLB-value between 8 and 15.

3. A pharmaceutical preparation according to claim 1, wherein said anthracenetriol active ingredient is contained in an amount of from 0.5–3 wt. %.

4. A pharmaceutical preparation according to claim 1, wherein said anthracenetriol contains the urea as a surfactant-urea combination in an amount which is 2 to 25 times the amount by weight of the anthracenetriol component.

5. A method of treating psoriasis by the short time method, which comprises
treating skin affected by psoriasis with an anti-psoriasis effective amount of a pharmaceutical preparation as set forth in claim 1, and
rinsing said skin with water, to thereby remove said preparation.

* * * * *